(12) United States Patent
Hassinen et al.

(10) Patent No.: US 6,971,506 B2
(45) Date of Patent: Dec. 6, 2005

(54) TEST TUBE CARRIER

(75) Inventors: Matti Hassinen, Espoo (FI); Juha Korhonen, Espoo (FI); Keijo Kaarakainen, Järvenpää (FI); Atte Mallenius, Kerava (FI)

(73) Assignee: Thermo Electron Oy, Vantaa (FI)

( * ) Notice: Subject to any disclaimer, the term of this patent is extended or adjusted under 35 U.S.C. 154(b) by 54 days.

(21) Appl. No.: 10/473,888

(22) PCT Filed: Apr. 3, 2002

(86) PCT No.: PCT/FI02/00287

§ 371 (c)(1),
(2), (4) Date: Oct. 2, 2003

(87) PCT Pub. No.: WO02/082095

PCT Pub. Date: Oct. 17, 2002

(65) Prior Publication Data
US 2004/0124109 A1 Jul. 1, 2004

(30) Foreign Application Priority Data
Apr. 3, 2001 (FI) .................................. 20010696

(51) Int. Cl.[7] .............................................. B65G 13/02
(52) U.S. Cl. ............................. 198/803.14; 198/867.11; 198/867.14
(58) Field of Search .................. 198/867.02, 867.06, 198/867.08, 867.11, 867.14, 867.12, 803.14, 198/803.15, 867.01

(56) References Cited

U.S. PATENT DOCUMENTS

| | | | |
|---|---|---|---|
| 3,918,920 A | 11/1975 | Barber | |
| 4,684,012 A * | 8/1987 | Feddersen | 198/867.05 |
| 4,807,421 A * | 2/1989 | Araki et al. | 198/867.05 |
| 5,224,585 A * | 7/1993 | Blanco et al. | 198/867.13 |
| 5,769,203 A * | 6/1998 | Marti Sala | 198/803.14 |
| 6,176,369 B1 * | 1/2001 | Petrovic | 198/867.11 |
| 6,274,092 B1 | 8/2001 | Itoh | |
| 6,343,690 B1 | 2/2002 | Britton et al. | |

FOREIGN PATENT DOCUMENTS

| | | |
|---|---|---|
| EP | 0 414 644 A2 | 2/1991 |
| EP | 0 469 390 A2 | 2/1992 |
| EP | 0 916 406 A2 | 5/1999 |

OTHER PUBLICATIONS

Patent Abstract of Japan, vol. 2000, No. 12, Jan. 3, 2001.

* cited by examiner

Primary Examiner—James R. Bidwell
(74) Attorney, Agent, or Firm—Birch, Stewart, Kolasch & Birch, LLP

(57) ABSTRACT

The invention relates to a test tube carrier (4) for transporting test tubes in a transport system, said carrier (4) comprising a base (8) having a recess made thereto for accommodating the bottom of a test tube/vial (1), and support members (9, 10) adapted to the carrier base (8) for clamping a test tube (1) inserted in said recess and supporting the same. The support members (9, 10) are permanently affixed to said carrier base (8) and comprise elongated portions with their free ends bent toward the vertical center axis of the carrier base and said upper ends providing a support surface (22) for making supportive contact to the test tube. The bottom of the carrier base recess for accommodating a test tube is advantageously made flat and the carrier base is provided with test tube support members whose support surfaces (22) extend to at least two different heights from the top level of the carrier base (8).

6 Claims, 3 Drawing Sheets

TEST TUBE CARRIER

This application is the national phase under 35 U.S.C. § 371 of PCT International Application No. PCT/FI02/00287 which has an International filing date of Apr. 3, 2002, which designated the United States of America.

BACKGROUND OF THE INVENTION

1. Field of the Invention

The invention relates to a test tube carrier according to the preamble of claim 1 for transporting different kinds of test tubes in sample analysis systems and other kinds of automatic specimen handling systems, wherein individual test tubes/vials are moved between separate stations.

2. Description of Background Art

These kinds of test tube carriers are conventionally used for transporting samples to be analyzed for probing at different analyzer stations. The sample transport system comprises a conveyor lane for moving the transport carriers and a number of carrier handling points, wherein the carrier with its test tube(s) can be moved to a sample probing point, a queue thereof or to a buffer station, for instance. The test tube carrier is provided with grooves and projections that supportingly mate the edges of the transport track so as to guide the travel of the carrier and secure its upright position. The travel of the test tubes is controlled by means of a bar code attached to the tubes, whereby the bar code must be readable at all handling stations irrespective of the tube and carrier positions.

A test tube carrier of the above-described kind is disclosed in Canadian Patent Application No. 2,216,052 related to a specimen transport system. The test tube carrier described in the publication has a central recess made to the round carrier base having thereabout adapted retainer members of thin, round steel wires that project upright from the base at the sides of the recess. The bottom end of a test tube is placed in the recess, whereby the steel-wire retainer members support the test tube from its sides. The lower end of the steel-wire retainer members supporting the test tube is bent in a Z-shape so that one end of the bent wire is inserted into a hole made in the carrier base, while the other end forms an upright oriented portion that supports the test tube. The lower end of the steel wire inserted in the hole of the carrier base is adapted freely rotatable in the hole and the upright-oriented portion of the wire is adapted in an arcuate control groove that guides the movement of the wire. The carrier base generally supports three steel-wire retainer members that are displaced symmetrically about the recess of the base. Below the tips of the upright-oriented portions of the steel-wire retainer members is adapted an O-ring serving to squeeze the wires toward the vertical center axis of the carrier base so that the wires are forced to follow the arcuate shape of the control groove while their lower ends rotate in the holes of the carrier base. When the test tube is inserted in the carrier, the steel-wire retainer members are urged apart from each other, and, having the test tube in place on the carrier, the O-ring clamps the steel-wire retainer members against the test tube.

The above-kind of test tube carrier, however, is hampered by plural disadvantages. Due to incorporating loosely moving members, difficult-to-clean recesses that may accumulate sample material and other impurities are formed, e.g., in the holes and control grooves of the steel-wire retainer members of the carrier base. As a result, the structure has a higher need for aggressive washing and disinfection, whereby the washing step becomes extremely arduous especially for the O-ring that must be replaced from time to time due to aging. If the compressive force exerted by the ring is lost or the ring breaks up, the test tubes will not stay upright at all on the test tube carrier. If the test tube flips aside during transport, the moving carriers contaminate the transport system over a large area, whereby a long shutdown is necessary for cleaning. Hence, the condition of the carriers must be continuously monitored during the operation of the transport system. The machining of the drilled holes and arcuate control grooves need two cutting steps per each steel-wire retainer member and, furthermore, an unnecessarily complicated casting mold for making the carrier base. The use of elongated steel-wire retainer members adapted to conform with the exterior surface of a test tube is also hampered by the problem of the wire members supporting the test tube only at one point unless the wire members are made extremely flexible. These support points do not readily coincide with each other at the same height of the test tube, whereby the test tube assumes a tipped position under the forces imposed thereto at the support points located at different heights. This problem can be overcome by shaping a conical or concave bottom for the recess drilled to the carrier base, whereby the shape of the recess bottom supports sufficiently the bottom end of the test tube with the penalty of having test tubes of the different size placed at different heights and making sample recovery and reading of identification information more difficult. If the retainer members are made from a material of such a high elasticity that the compressive force imposed by the O-ring can press them along their entire length against the exterior surface of the test tube, the wires generally become so thin that the risk of damage thereto in the insertion and removal of test tubes becomes substantial. Inasmuch the lower ends of the steel-wire retainer members and their drilled support holes must be located close to the periphery of the carrier base, the base must be made high, because the transport system guide grooves of base cannot be located within the portion of the carrier base occupied by the holes drilled for the retainer members. As a result, the transport system guide grooves of the carrier base must be made to the bottom portion of the base, wherein they give inferior guidance to the travel of the test tube carrier than if the guide grooves were located at a higher elevation from the bottom portion of the test tube carrier.

SUMMARY AND OBJECTS OF THE INVENTION

It is an object of the present invention to provide a test tube carrier featuring secure support to test tubes inserted into a predetermined position and having no loosely moving members.

The goal of the invention is achieved by way of adapting in a fixed fashion to the sides of the carrier base recess such elastic members that offer a support surface for a test tube inserted therebetween.

According to a preferred embodiment of the invention, the test tube carrier has made thereto a flat-bottom recess for accommodating a test tube and there are two elastic members adapted above one another so that their support surfaces are located at different levels from the carrier base.

The invention offers significant benefits.

A test tube carrier according to the invention has no loosely moving parts, whereby its wear in use and need for maintenance are minimal. As the structure has no loosely moving parts, it can be designed free from any recesses or holes capable of accumulating contaminating material.

Accordingly, the test tube carrier is easy to clean and keep in a hygienic condition. The test tube carrier operates problem-free at all times and possible damage in its structure is instantly visible. The base part of the test tube carrier can be manufactured advantageously by injection molding without any need for post-machining, and the device is extremely simple to produce by manual techniques or in automatic assembly systems. The test tube carrier operates reliably over a large range of test tube/vial sizes and the bottom of the recess made in the base part thereof for supporting the test tube bottom can be flat, whereby the test tube/vial will assume at all times an equal height and a correct alignment guided by the elastic support members. The elastic support members can be advantageously made from spring steel band, whereby they become sufficiently stiff for holding test tubes in a reliable fashion. The location of the elastic support members does not curtail the degree of freedom in the shaping of the exterior surface of the carrier base part thus allowing the guide grooves to be made deeper in order to reduce the swaying of the carrier during its travel. The elastic support members cope with test tubes of varying dimensions and shapes as allowed within their manufacturing tolerances so as to keep the test tubes firmly gripped by the elastic support members.

Further scope applicability of the present invention will become apparent from the detailed description given hereinafter. However, it should be understood that the detailed description and specific examples, while indicating preferred embodiments of the invention, are given by way of illustration only, since various changes and modifications within the spirit and of the scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

In the following, the invention will be examined in greater detail with the help of exemplary embodiments illustrated in the appended drawings in which.

DETAILED DESCRIPTION OF THE PREFERRED EMBODIMENTS

Figure 1:
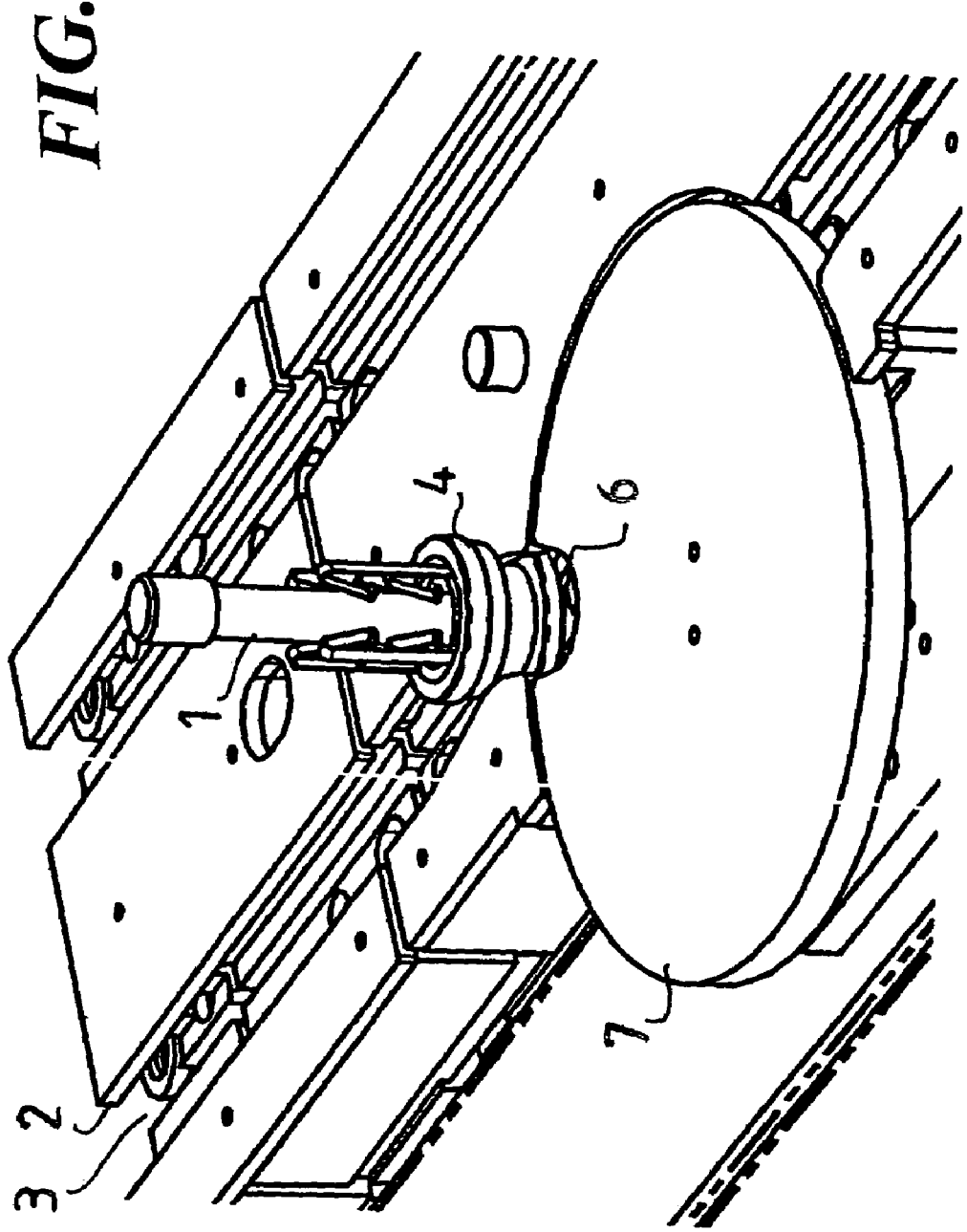
FIG. 1 shows a test tube carrier according to the invention in its operating environment.

Referring to FIG. 1, therein is shown a portion of a transport system suited for moving test tubes 1 placed on test tube carriers 4 between different handling stations. The transport system comprises a guide lane 3 forming a transport path for the test tube carriers 4 and having rails 2 at its sides for supporting the test tube carriers during their travel and preventing the same from tipping aside. At the bottom of the guide lane 3 are provided running belts 5 (not shown) on which the test tube carriers move supportedly. The guide lane 3 forming the transport path controls the transport route of a given test tube carrier 4. Operating along the path of the guide lane are adapted handling stations capable of performing analysis of a sample contained in a test tube, rearrangement of the sample sequence and other possible functions such as derouting to a crossing lane. In the transport system of FIG. 1, the handling station shown therein includes a turnstile disc 7 with a transfer slot 6 for receiving a test tube carrier 4. The test tube carrier 4 has a rotation-symmetric shape that mates with the compatible shape of the transfer slot. When a test tube carrier 4 comes to the handling station, the carrier meets a transfer slot 6, whereby it can be picked off from the lane by means of rotating the disc 7 to an analyzer for instance. Simultaneously, the solid periphery of disc 7 prevents successive test tube carriers from passing forward during the time the transfer slot is rotated off from lane 3. As the function and structure of the transport system is not essentially related to the present invention, its detailed description need not be discussed further herein.

Figure 2:
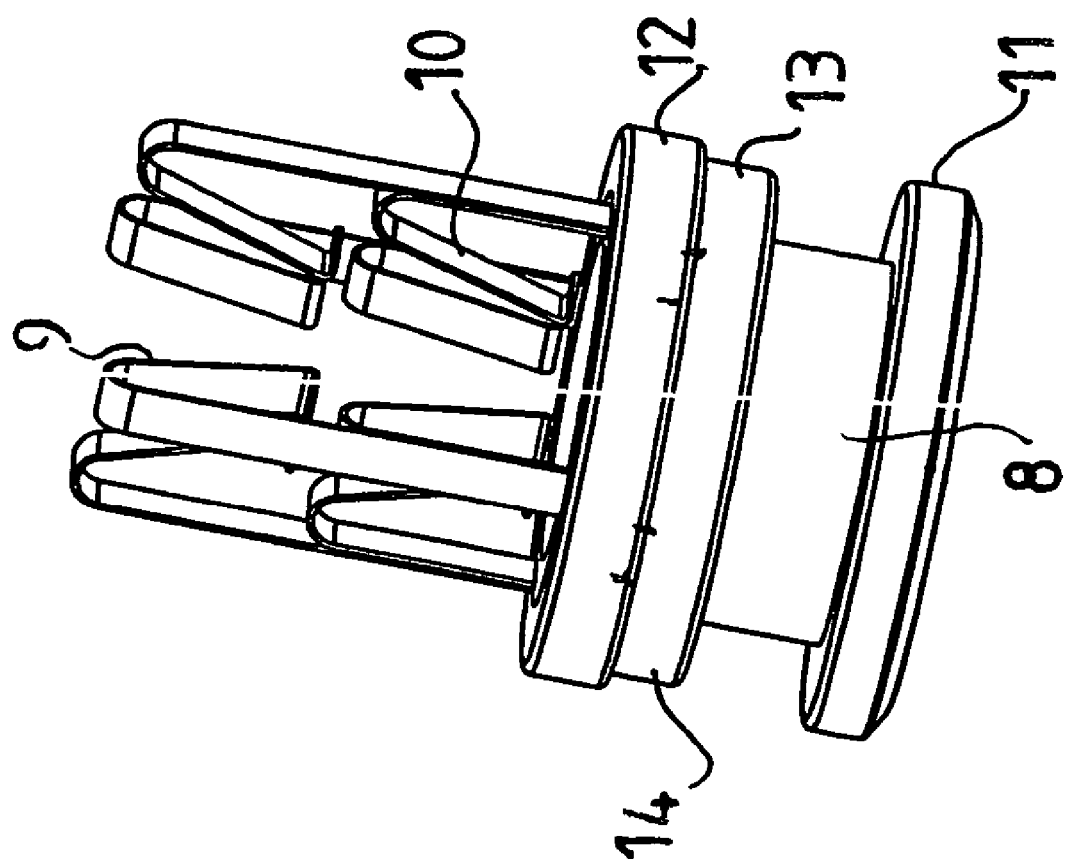
FIG. 2 shows a perspective view of the embodiment of FIG. 1.
Figure 3:
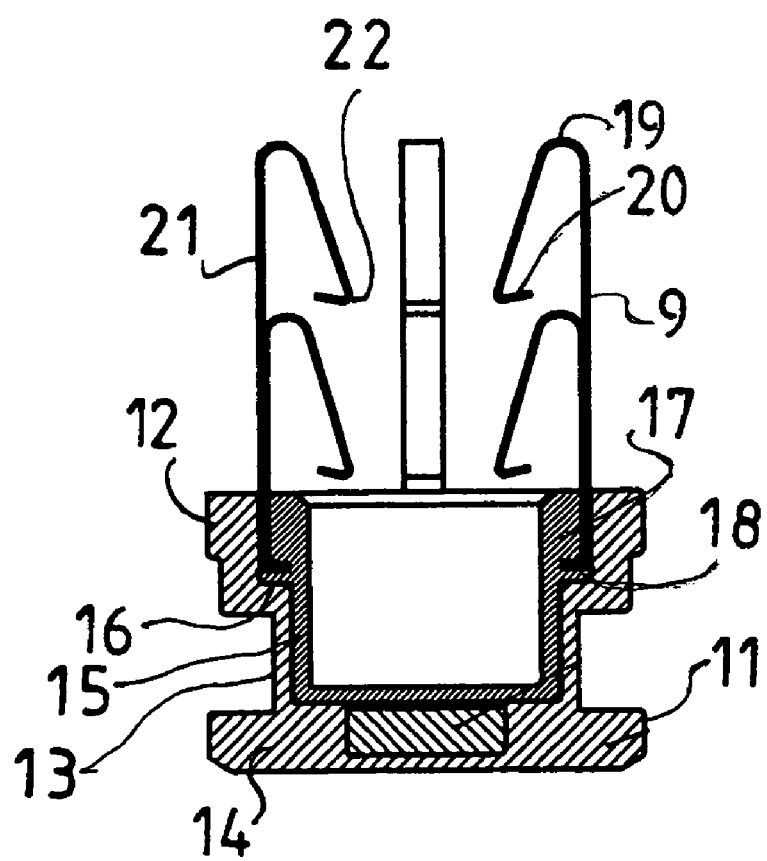
FIG. 3 shows a cross-sectional view of the embodiment of FIG. 2.

In FIGS. 2 and 3 is shown an embodiment of the test tube carrier 4 according to the invention. This kind of test tube carrier is intended for use in conjunction with test tubes of dia. 10 to 17 mm. The test tube carrier comprises a base 8 with elastic support members 9, 10 affixed to the base. The base 8 has a rotation-symmetric shape and has its lower portion and upper portion provided with glide faces 11, 12 adapted to supportedly mate with the edges of the transport system guide lane 3. Above the lower glide face 11 is located a guide groove 13 that mates with the shape of the guide rails 2 of transport system guide lane 3. Above the guide groove 13 is first made a narrow face 14 for optic indicia and then above the narrow face 14 is located an upper glide face 12. Obviously, the exterior design of a test tube carrier according to the invention is not limited by the exemplary embodiment described herein, but rather, the actual contour of the test tube carrier must be made compatible with the structure of the transport lane. The base 8 of the test tube carrier is formed by two parts, namely, an outer shell 14 and a cup part 15 adapted to fit therein. The bore of the outer shell is machined to so as have a recess whose interior diameter is smaller that the inner rim portion of the outer shell 14 extending to the top level of the outer shell 14, whereby a shoulder 16 is formed into the outer shell bore. The outer rim of the cup part 15 is made compatible with this shape of the outer shell bore so that the cup part has a larger rim portion 17 fitting snugly in the large-diameter portion of the outer shell bore. The center recess bore of the cup part 15 has a straight cylindrical inner wall with a flat bottom. In a ready-assembled test tube carrier, these two parts are put together concentrically so that their top rims are in the same plane. In practice, these parts can be made from polymer materials by injection molding, for instance. Since, the test tube carrier is not subjected to major mechanical stress, it may also be fabricated from any other easy-to-clean material.

In a side view, the elastic support members 9, 10 resemble the shape of a fishing hook. Typically, the support members are made from stainless steel band or any similar elastic and durable material. Each elastic support member comprises a single contoured strip having a right angle bend 18 made to its one end. To the opposite end of the member in regard to bend 18 is contoured a smooth arc so that the strip terminates at a finger portion 19 directed toward the right-angle bend 18 and at its end an inward hook tip 20 pointed toward the inside surface of the finger portion. The convex edge of the hook tip acts as a supporting surface 22 that rests against the periphery of an inserted test tube/vial, and this convex edge surface is advantageously oriented in a direction perpendicular to the center axis of the test tube and the vertical center axis of the base, whereby it will form a point-like contact to the round surface of the test tube periphery. The upper set 10 of elastic support members is made longer than the lower set. The spring function of these elastic support members 9, 10 is provided by the resilience of the long straight portion 21 between the bent portions and the long bend of the finger portion. In this fashion the straight portion can be made longer by having the finger portion 19 bent downward toward the carrier base 8.

In the illustrated embodiment, the number of elastic support members 9, 10 is eight, whereby they are superposed pairwise above one another in two concentric circles at 90° spacing from each other. The superposed support members are placed inside one another so that the shorter member 9 is innermost thus aligning the hook portions of members 9 and 10 above one another in the vertical direction. The outer surface of the cup part 15 of the carrier base is provided with grooves suited to accommodate the elastic support members and having at the ends of the grooves recesses suited to accommodate the right-angle bent end 18 of the elastic support members 9, 10. In the assembly of the test tube carrier, the elastic support members 9, 10 are first inserted in the grooves of the cup part, whereupon the cup part 15 with its elastic support members is pressed into the bore of the outer shell 14 to complete the assembly. The seam between the outer shell 14 and the cup part 15, as well as the root of the elastic support members is secured with a sealant, for instance, whereby the test tube carrier is finished free from any crevices capable of accumulating contamination and the locking of the carrier members to each other is assured. Resultingly, the elastic support members become an integral part of the test tube carrier. During the assembly step, between the outer shell 14 and the cup part 15 is placed a so-called RFID tag memory chip that can receive the identification data of the test tube specimen over a radio-frequency link and then provide the read-out of the data at any time so desired.

Without departing from the scope and spirit of the present invention, embodiments different from those described above may be contemplated.

For instance, the carrier body could be made from several parts, but this option only makes its manufacture more complicated and costlier. The number of elastic support member pairs may be varied from 3 to 5, in certain applications up to 6 pairs, with the penalty that the greater number of elastic support members may complicate the read-out of test tube/vial identification indicia, such as a bar code, by automatic detection means. If the bottom of the carrier base is provided with a conical or concave recess, it is feasible to use only one elastic support element instead of a pair of support members in each support member position, whereby a test tube/vial inserted in a carrier is supported by said conical recess and only one ring of the elastic support elements. This arrangement, however, eliminates the benefit achievable by the flat bottom of the test tube recess in the carrier. The elastic support elements need not necessarily be placed interposed with each other, but if the support members are staggered about the periphery of the carrier base, difficulties will be encountered in the readout of test tube indicia and assembly of the test tube carrier. Obviously, the elastic support elements do not necessarily have a downward directed hook portion, but their free ends may as well be directed first toward the vertical center axis of the carrier base and then upward. The hooked tip may be bent outwardly at the upper end of the support member or, alternatively, coiled into a ring.

The invention being thus described, it will be obvious that the same may be varied in many ways. Such variations are not to be regarded as a departure from the spirit and scope for the invention, and all such modifications as would be obvious to one skilled in the art are intended to be included within the scope of the following claims.

The end of the elastic support elements facing the test tube/vial is advantageously shaped so as to provide at the contact point a horizontally lineal support surface 22 that makes only a point-like contact to the periphery of the test tube, whereby the support given thereto becomes well-defined. However, this kind of a straighter support member lacking the hooked portion offers less elasticity with the same band material thickness and makes the of the support member tips look sharper which may give a less user-friendly impression. While the elastic support elements are advantageously made in the above-described fashion from a flat band material, also other continuous sections such as tubular blanks may be contemplated as the raw material of the elastic members.

What is claimed is:

1. A test tube carrier for transporting test tubes in a transport system, said carrier comprising
    a base having a recess made thereto for accommodating the bottom of a test tube/vial; and
    support members adapted to the carrier base for clamping a test tube inserted in said test tube recess and supporting the same, said support members being permanently affixed to said carrier base and comprising elongated portions with their free ends bent toward the vertical center axis of the carrier base and said upper ends providing a support surface for making supportive contact to the test tube, characterized in that wherein the support surface of said support members is arranged to extend to at least two different heights from the top level of the carrier base and said carrier base being assembled from two concentrically insertable parts leaving therebetween recesses into which the lower ends of said support members are permanently affixed.

2. The test tube carrier of claim 1, the bottom of said test tube recess is flat.

3. The test tube carrier of any one of foregoing claims, wherein the upper end of said support members include a hooked finger portion directed toward the vertical center line of the carrier base and then toward the carrier base.

4. The test tube carrier of claim 3, wherein said support members are made from a flat band material.

5. The test tube carrier of claim 3, wherein said support surface forms a horizontally lineal contact surface aligned perpendicular to the center axis of the test tube.

6. The test tube carrier of claim 4, wherein said support surface forms a horizontally lineal contact surface aligned perpendicular to the center axis of the test tube.

* * * * *